US00PP35049P2

(12) United States Plant Patent
Ranney et al.

(10) Patent No.: US PP35,049 P2
(45) Date of Patent: Mar. 21, 2023

(54) ***RHODODENDRON* PLANT 'NCRX10'**

(50) Latin Name: ***Rhododendron* hybrid**
Varietal Denomination: 'NCRX10'

(71) Applicant: North Carolina State University, Raleigh, NC (US)

(72) Inventors: Thomas Green Ranney, Arden, NC (US); Darren H. Touchell, Arden, NC (US); Andra Windorf Nus, Arden, NC (US); Irene Palmer, Arden, NC (US); Nathan Lynch, Arden, NC (US)

( * ) Notice: Subject to any disclaimer, the term of this patent is extended or adjusted under 35 U.S.C. 154(b) by 0 days.

(21) Appl. No.: 17/845,491

(22) Filed: Jun. 21, 2022

(51) Int. Cl.
*A01H 5/00* (2018.01)
*A01H 6/36* (2018.01)

(52) U.S. Cl.
USPC ..... Plt./238

(58) Field of Classification Search
USPC ..... Plt./227, 238
See application file for complete search history.

*Primary Examiner* — Karen M Redden
(74) *Attorney, Agent, or Firm* — Cassandra Bright

(57) ABSTRACT

A new and distinct cultivar of *Rhododendron* plant named 'NCRX10' is disclosed, characterized by a compact habit, and large semi-double, coral pink flowers in spring that rebloom in early fall. The new cultivar is a *Rhododendron*, suitable for ornamental garden purposes.

2 Drawing Sheets

Figure 1:
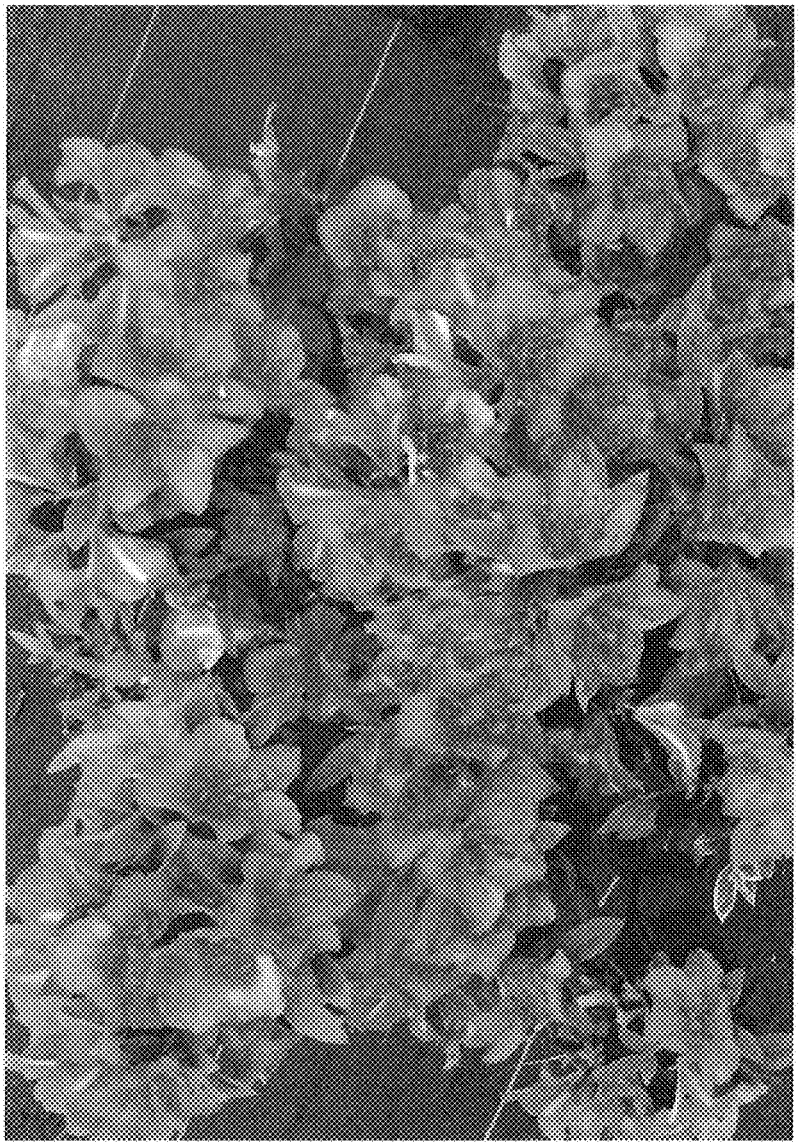

Latin name of the genus and species: *Rhododendron* hybrid.

Variety denomination: The inventive hybrid was selected from seedlings derived from a controlled cross between evergreen azaleas 'H2008-231-024' (female, unpatented experimental hybrid) and 'H2008-231-006' (male, unpatented experimental hybrid). Prior to the designation of the varietal denomination, 'NCRX10' was referred to by its experimental code: 'H2013-169-004'.

BACKGROUND OF THE INVENTION

The present invention comprises a new and distinct hybrid evergreen azalea cultivar hereinafter referred to by the cultivar name 'NCRX10'. This hybrid azalea was developed by a controlled breeding program in Mills River, N.C. The cross resulting in the new variety was conducted during the Spring of 2012. 'NCRX10' was selected for its semi-double, coral pink flowers, floriferousness, dense and compact growth habit, and consistent reblooming. It was selected from the controlled, hand pollination of emasculated female experimental hybrid 'H2008-231-024' (unpatented) and male/pollen parent experimental hybrid 'H2008-231-006' (unpatented). 'NCRX10' was first selected from this population of seedlings during the Summer of 2015.

Container trials were conducted using pine bark media supplemented with 1.04 kg·m-3 dolomitic lime, 0.74 kg·m-3 granulated micronutrients and top-dressed with 5- to 6-month slow-release fertilizer (15-9-12). Full-sun field trials were conducted in plastic-covered, bark-amended clay soils with minimum winter temperatures of −2° F. (−19° C.) and maximum summer temperatures 98° F. (37° C.).

The first asexual propagation of 'NCRX10' occurred in 2015 by rooting stem cuttings at a research nursery in Mills River, N.C. 'NCRX10' roots readily from firm softwood cuttings treated with a basal dip of 3,000 ppm indole butyric acid (potassium salt) in water. 'NCRX10' has been found to retain its distinctive characteristics through successive asexual propagations over 6 years.

SUMMARY OF THE INVENTION

The following are the unique combination of characteristics of this new cultivar when grown under standard horticultural practices at a research nursery in Mills River, N.C.

1. Floriferous spring display.
2. Large, coral pink, semi-double flowers.
3. Dense, compact habit.
4. Consistent fall reblooming.

COMPARISON TO PARENT VARIETIES

'NCRX10' is similar in most horticultural characteristics to the seed parent. Plants of the new cultivar 'NCRX10' however differ in the following:

1. The new variety has bright coral-pink flowers, while the seed parent has light pink flowers.
2. The new variety has semi-double flowers, while the seed parent has single flowers.

'NCRX10' is similar in most horticultural characteristics to the pollen parent. Plants of the new cultivar 'NCRX10' however differ in the following:

1. Flowers of the new variety are semi-double, while flowers of the pollen parent are fully-double.
2. The new variety has bright, coral-pink flowers, while the pollen parent has bright pink flowers.

COMMERCIAL COMPARISON

'NCRX10' can be compared to the commercial variety *Rhododendron* 'Conled', U.S. Plant Pat. No. 10,568. Plants of the new cultivar 'NCRX10' are similar to plants of 'Conled' in most horticultural characteristics. Plants of the new cultivar 'NCRX10', however, differ in the following:

1. Flower color of the new variety is RHS Strong Purplish Red 54A, while the flower color of this comparator is Deep Pink RHS 48B.
2. Flowers of the new variety are semi-double with petaloids, while flowers of this comparator are single.
3. Mature plants of the new variety are larger than mature plants of this comparator.

BRIEF DESCRIPTION OF THE PHOTOGRAPHS

'NCRX10' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

FIG. 1 Image showing high floral coverage in 3-gallon containers; image taken from 3-year-old container plants grown in Grand Haven, Mich., in 2020.

Figure 2:
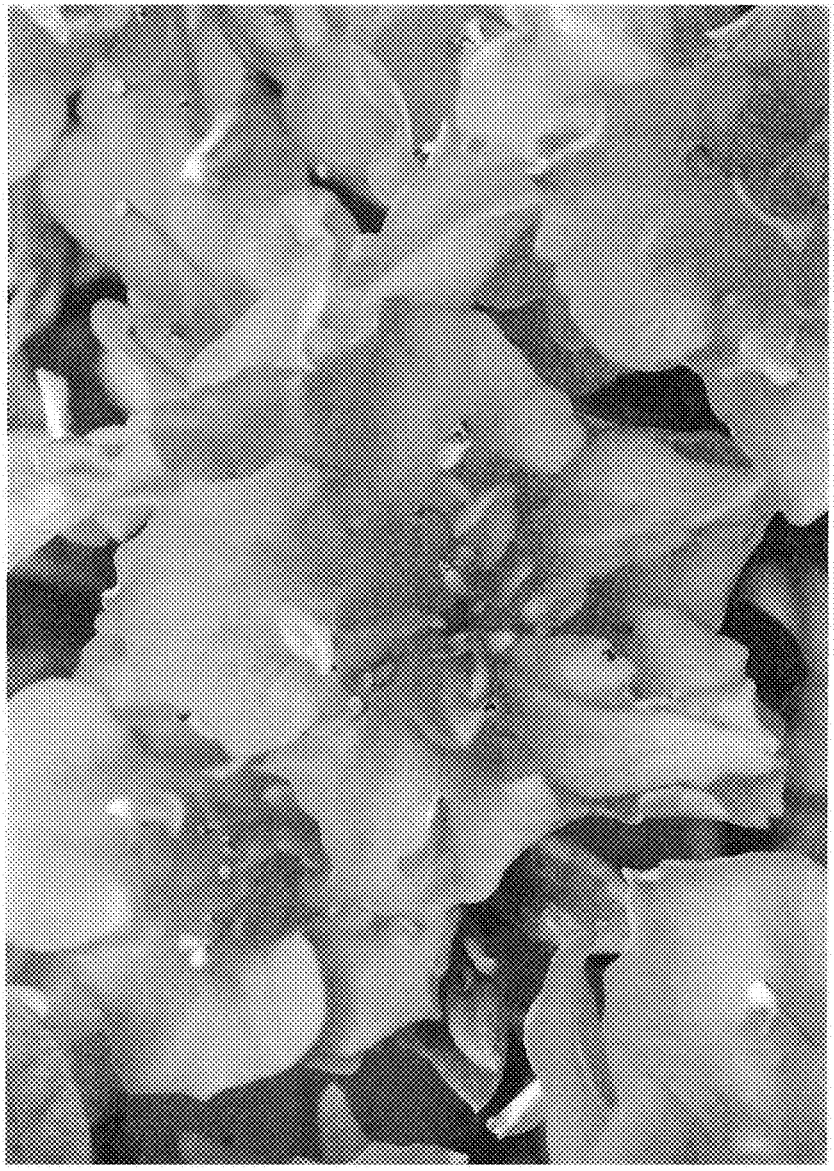

FIG. 2 Image showing a close-up of semi-double bright pink (RHS 54A) flowers in a 3-gallon container. Image taken from 3-year-old container plants grown in Grand Haven, Mich., in 2019.

DETAILED BOTANICAL DESCRIPTION

The following is a detailed description of the botanical characteristics of the new and distinct hybrid evergreen azalea known by the denomination 'NCRX10'. The detailed description was taken on a 2-year-old container-grown plant in Mills River, N.C., in 2021. Where pertinent, descriptive data was supplemented by observations/measurements taken on a 6-year-old individual located in field trials in Mills River, N.C., as well as information provided from cooperators in Grand Haven, Mich. All colors cited herein refer to The Royal Horticultural Society Colour Chart (The Royal Horticultural Society (R.H.S.), London, Sixth Edition (2015). Where specific dimensions, sizes, colors, and other characteristics are given, it is to be understood that such characteristics are approximations or averages set forth as accurately as is practicable.

Botanical classification: *Rhododendron* hybrid 'NCRX10'.

PROPAGATION

Typical method: Softwood cuttings.

Root description: Dense, fibrous, freely branching, thin to medium texture. White to brown, not accurately measured with an R.H.S. chart.

Time to initiate rooting: 6 to 8 weeks.

Time to produce a rooted young plant: 12 to 16 weeks at 18 to 27° C.

PLANT

Plant type: Evergreen azalea.

Growth habit: Dense, globose.

Height: 90 to 120 cm.

Width: 90 to 150 cm.

Growth rate: Moderate.

Shoots (current year's growth):
- *Length.*—Average About 6.0 cm (4 to 9 cm).
- *Diameter.*—About 0.3 cm.
- *Color.*—Strong Yellow Green (RHS 144C).
- *Texture.*—Pubescent.

Shoots (prior year's growth):
- *Length.*—About 10 cm.
- *Diameter.*—About 0.5 cm.
- *Color.*—Strong Yellow Green (RHS 144C).
- *Texture.*—Pubescent.

Branches (woody branches 2-4 years old):
- *Length.*—About 10 cm.
- *Diameter.*—About 0.5 to 1.0 cm.
- *Color.*—Dark Greyish Yellowish Brown (RHS N199B).
- *Texture.*—Glabrous with vertical fissures.

Internode length: Average 1 cm (0.5 to 2 cm).

FOLIAGE

Leaf:
- *Type.*—Simple, evergreen.
- *Arrangement.*—Alternate.
- *Shape.*—Ovate.
- *Apex.*—Mucronate.
- *Base.*—Cuneate.
- *Margin.*—Entire, ciliate.
- *Venation.*—Reticulate.

Emerging leaf:
- *Color.*—Upper surface: Strong Yellow Green (RHS 144A). Lower surface: Strong Yellow Green (RHS 143C).
- *Texture.*—Upper surface: Pubescent. Lower surface: Pubescent.

Mature leaf:
- *Length.*—About 4.0 cm (3.2 to 5.0 cm).
- *Width.*—About 2.4 cm (1.8 to 3.0 cm).
- *Color.*—Upper surface: Greyish Olive Green (RHS NN137A). Lower surface: Moderate Yellowish Green (RHS 138A).
- *Texture.*—Upper surface: Pubescent. Lower surface: Pubescent.

Fall/winter leaf:
- *Color.*—Upper surface: Dark Greyish Reddish Brown (RHS 200A). Lower surface: Greyish Yellow Green (RHS 194A) with blotches of Dark Greyish Yellowish Brown (RHS N199B).

Leaf attachment: Petiolate.

Petiole:
- *Length.*—About 1.0 cm.
- *Diameter.*—About 0.2 cm.
- *Color.*—Moderate Yellow Green (RHS 147B).
- *Texture.*—Pubescent.

FLOWER

Inflorescence:
- *Type.*—Congested terminal raceme (truss).
- *Flowering season.*—Mid-spring (mid-April-early May into June) reblooms in early fall (late September through October).
- *Flowering habit.*—Free-flowering.
- *Flower number.*—2-5 flowers per truss.
- *Consistency in display.*—Blooms reliably in the spring and consistently reblooms in the fall.
- *Lastingness of flowers.*—Each flower lasts approximately 3-7 days.
- *Fragrance.*—None.
- *Self-cleaning or persistent.*—Self-cleaning.

Truss bud:
*Length*.—About 1.0 to 1.8 cm.
*Diameter*.—About 0.5 to 0.8 cm.
Bud scales:
*Number*.—4 to 7.
*Length*.—About 0.8 to 1.2 cm.
*Width*.—About 0.5 to 1.0 cm.
*Color*.—Moderate Yellow Green (RHS 146D).
*Texture*.—Upper side is pubescent at tip; lower side is glabrous.
Emerging flowers:
*Shape*.—Elliptic, acuminate.
*Length*.—2.5 to 3.0 cm.
*Diameter*.—2 cm.
*Color*.—Strong Red (RHS 51A).
*Texture*.—Glabrous.
Perianth:
*Shape*.—Funnel-shaped, semi-double.
*Depth*.—About 3.5 cm.
*Diameter at anthesis*.—7.1 cm (6.0 to 8.0 cm).
*Arrangement*.—Whorled.
*Aspect*.—Facing upwards and outwards.
*Attachment*.—Pedicellate.
Petals:
*Outer petals*.—Number: 5 petals. Length: 4.0 to 5.0 cm. Width: 3.0 to 4.0 cm. Shape: Obovate. Apex: Obtuse. Base: Fused. Margin: Entire, undulate. Color: Color is consistent from opening to anthesis. Upper: Strong Purplish Red (RHS 54A). Lower: Strong Purplish Red (RHS 54A). Texture: Glabrous.
*Inner petaloids*.—Number: 4 to 7. Length: About 2.0 cm. Width: About 1.0 cm. Shape: Irregular. Apex: Inconsistent, often fused with a modified stamen. Base: Fused. Margin: Entire. Color: Upper: Strong Purplish Red (RHS 54A). Lower: Strong Purplish Red (RHS 54A). Texture: Glabrous.
Sepals:
*Number*.—5.
*Length*.—0.5 to 1.0 cm.
*Width*.—0.2 to 0.4 cm.
*Shape*.—Lanceolate.
*Apex*.—Cuneate.
*Margin*.—Ciliate.
*Color*.—Strong Yellow Green (RHS 145A).
*Texture*.—Pubescent.
Pedicels:
*Shape*.—Rounded.
*Length*.—About 1 cm.
*Diameter*.—About 0.2 cm.
*Color*.—Strong Purplish Red (RHS 54A).
*Texture*.—Pubescent.

REPRODUCTIVE ORGANS

Gynoecium:
*Pistil number*.—1.
*Pistil length*.—3.5 to 5.0 cm.
*Stigma shape*.—Orbicular to elliptic.
*Stigma length*.—About 0.1 cm.
*Stigma width*.—About 0.1 cm.
*Stigma color*.—Deep Red (RHS 53A).
*Style length*.—3.0 to 4.5 cm.
*Style diameter*.—About 0.1 cm.
*Style color*.—Strong Purplish Red (RHS 54A).
*Ovary shape*.—Ovate.
*Ovary length*.—About 0.5 cm.
*Ovary diameter*.—About 0.4 cm.
*Ovary color*.—Moderate Yellow Green (RHS 146B).
*Texture*.—Pubescent.
Androecium:
*Stamen number*.—5 to 10.
*Anther shape*.—Ovoid with two apical pores.
*Anther attachment*.—Dorsifixed.
*Anther length*.—About 0.1 cm.
*Anther width*.—About 0.1 cm.
*Anther color*.—Dark Red (RHS 183A).
*Filament length*.—2.5 to 4.0 cm.
*Filament diameter*.—About 0.1 cm.
*Filament color*.—Strong Purplish Red (RHS 54A).
*Amount of pollen*.—Normal.
*Pollen type*.—Thread-like.
*Pollen color*.—Greenish White (RHS NN155C).

OTHER CHARACTERISTICS

Fruit:
*Type*.—Capsule.
*Length*.—About 0.6 to 1.0 cm if successfully pollinated, about 0.4 cm if not.
*Diameter*.—About 0.5 to 1.0 cm if successfully pollinated, about 0.4 cm if not.
*Color*.—Immature fruit color: Strong Yellow Green (RHS 145A). Mature fruit color: Moderate Brown (RHS 200D).
*Texture*.—Pubescent.
Seed:
*Number*.—0 to hundreds per capsule.
*Length*.—Approximately 0.1 cm.
*Diameter*.—Approximately 0.05 cm.
*Color*.—Moderate Orange Yellow (RHS 164B).
*Texture*.—Glabrous.
Disease and pest resistance: Not observed to be susceptible nor resistant to normal diseases and pests of *Rhododendron*.
Temperature tolerance: Has been reliably cold hardy in USDA 6B.

What is claimed is:

1. A new and distinct cultivar of *Rhododendron* plant named 'NCRX10' as herein illustrated and described.

* * * * *